United States Patent
Heald et al.

(10) Patent No.: US 9,358,349 B2
(45) Date of Patent: Jun. 7, 2016

(54) GUIDING ASSEMBLY FOR INTRADERMAL INJECTION

(75) Inventors: Michael Heald, Berkshire (GB);
Timothy Salmon, Bridgewater, NJ (US)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 0 days.

(21) Appl. No.: 14/370,249

(22) PCT Filed: Jan. 10, 2012

(86) PCT No.: PCT/EP2012/050322
§ 371 (c)(1),
(2), (4) Date: Jul. 2, 2014

(87) PCT Pub. No.: WO2013/104414
PCT Pub. Date: Jul. 18, 2013

(65) Prior Publication Data
US 2015/0025458 A1  Jan. 22, 2015

(51) Int. Cl.
*A61M 5/42* (2006.01)
*A61M 5/32* (2006.01)
*A61M 5/46* (2006.01)

(52) U.S. Cl.
CPC ............ *A61M 5/425* (2013.01); *A61M 5/3287* (2013.01); *A61M 5/46* (2013.01); *A61M 2210/04* (2013.01)

(58) Field of Classification Search
CPC ... A61M 5/3243; A61M 5/3287; A61M 5/42; A61M 5/425; A61M 5/427; A61M 5/46
See application file for complete search history.

(56) References Cited

U.S. PATENT DOCUMENTS

| 5,242,453 | A | * | 9/1993 | Gubich ...................... 604/115 |
| 2007/0232994 | A1 | | 10/2007 | Sonoda et al. |
| 2009/0204102 | A1 | | 8/2009 | Alchas |

FOREIGN PATENT DOCUMENTS

| DE | 387465 C | 1/1924 |
| EP | 0526986 | 2/1993 |
| EP | 0887083 | 12/1998 |
| EP | 1787584 | 5/2007 |
| EP | 2404547 | 1/2012 |
| WO | 98/19726 | 5/1998 |
| WO | WO 02/100276 | 12/2002 |
| WO | 2010/018411 | 2/2010 |
| WO | WO 2010/087524 | 8/2010 |

OTHER PUBLICATIONS

Machine translated version of applicant cited reference—Schirrmacher, Roland Dipling (EP0887083).*
Machine translated version of applicant cited reference—Agostino G Rossi DR (DE387465).*
International Search Report for Int. App. No. PCT/EP2012/050322, completed Nov. 5, 2012.

* cited by examiner

*Primary Examiner* — Bhisma Mehta
*Assistant Examiner* — James D Ponton
(74) *Attorney, Agent, or Firm* — Fish & Richardson P.C.

(57) ABSTRACT

Described is a guiding assembly for an injection device comprising a mount adapted to receive an injection device, a first gripping member rotatably coupled to the mount, a first lateral stop member coupled to the first gripping member, and a spring biasing the first gripping member in a first angular position.

19 Claims, 5 Drawing Sheets

GUIDING ASSEMBLY FOR INTRADERMAL INJECTION

CROSS REFERENCE TO RELATED APPLICATIONS

The present application is a U.S. National Phase Application pursuant to 35 U.S.C. §371 of International Application No. PCT/EP2012/050322 filed Jan. 10, 2012, the contents of which are fully incorporated herein by reference.

TECHNICAL FIELD

The present invention relates to a guiding and/or adjustment assembly for an injection device being particularly adapted and intended for intradermal injection.

Some medicaments require injection into the dermal layer of the skin. Since the dermal layer is comparatively thin and typically comprises a thickness between 2 and 3 millimeters and is further located below or underneath the epidermis, injection of medicaments into the dermal layer is rather challenging and requires respective skills of the medical staff or a respective user.

BACKGROUND

From document US 2009/0204102 A1 a method is for instance known for using a needle assembly for an intradermal injection. There, a drug delivery device is provided including a needle cannula and a limiter surrounding the needle cannula. The device further includes a skin engaging surface on the limiter, wherein the limiter is movable from a first position in which an elongated portion of the needle cannula is exposed for access to a medication vial, to a locked second position in which the limiter is not movable from the second position to the first position. In said second position, the needle tip extends beyond the skin engaging surface a distance of about 3 min or less. This particular needle assembly requires mutual interaction of various mechanical components in order to provide a required locking or stopper mechanism.

It is therefore an object of the present invention to provide a rather simple and efficient means to facilitate intradermal injection, in particular by making use of conventional injection devices like syringes or pen-type injectors. Moreover, the solution should be cost efficient in production and should serve as an extension or as an additional module to be coupled with existing injection devices for preparing and/or adapting the same for intradermal injection purposes.

SUMMARY

In a first aspect, the invention provides a guiding and/or adjustment assembly for an injection device. The guiding assembly comprises a mount for the injection device, which in turn comprises a piercing assembly, preferably in form of an injection needle, cannula or the like. The piercing assembly of the injection device points in a distal direction with a tipped end, hence towards the skin to be pierced by the piercing assembly. The guiding assembly further comprises at least a first lateral stop member arranged at a pre-defined lateral distance sidewards from the piercing assembly and is further adapted to provide a support for the skin to be pierced by the piercing assembly. In this context, lateral direction or distance refers to the radial direction with respect to the elongation of the piercing assembly, defining the respective axial direction.

The lateral distance between the stop member and the tipped end of the piercing assembly defines a depth of deposition for an injectable medicament underneath the surface of the skin. Hence, the lateral stop member is intended to provide a skin engaging surface, against which a pinched or bulged portion of penetrable skin is squeezed. By forming a pinched, squeezed or bulged skin section laterally abutting against the at least first lateral stop member, the respective skin layers raise and become reoriented by approximately 90°. In the bulged skin section to be established by means of the at least first lateral stop member, skin depth extends in a substantially lateral direction, that is parallel to the piercing assembly.

By having the tipped end of the piercing assembly arranged at a pre-defined lateral distance from the first lateral stop member, the needle or piercing assembly can penetrate the skin layer of interest in a precise and well-defined way for depositing the medicament at pre-determined injection depth underneath the skin.

The at least first lateral stop member provides a kind of reference point or reference surface with respect to the tipped end of the needle or piercing assembly and therefore facilitates intradermal injection. Hence, by forming a bulged or pinched skin section, the intradermal layer at least in sections substantially extends in axial direction, that is parallel to the elongation of the piercing assembly. Penetration depth of the piercing assembly into the bulged portion of the dermal tissue or skin therefore becomes almost irrelevant because the needle extends almost parallel to the dermal layer. In the bulged or pinched skin section it is predominantly the lateral distance between the lateral stop member and the tipped piercing assembly that directly corresponds to the depth of deposition or depth of injection for the injectable medicament underneath the peripheral surface of the skin.

According to a preferred embodiment, the at least one lateral stop member at least in sections extends substantially parallel to the tipped piercing assembly. Preferably, the piercing assembly in form of an injection needle extends in axial direction and the at least one lateral stop member at its distal free end comprises a skin engaging surface extending substantially parallel, even and/or flat shaped in axial direction.

According to another preferred embodiment, the injection device and the at least one lateral stop member are moveably disposed with respect to each other in direction of the longitudinal axis of the piercing assembly. This way, intradermal injection can be conducted in two subsequent steps. In a first step, a pinched or bulged skin section is formed by squeezing the respective skin section in lateral direction against the at least first lateral stop member. During this squeezing or pinching step, the piercing assembly is retracted and/or is already disposed in an idle position with its tipped end located at a distance from the peripheral surface of the skin section. After forming the bulged skin section, in a second step, the injection device, or at least its piercing assembly, is slidably disposed and driven in distal direction for penetrating a particular skin layer and for dispensing a pre-defined amount of the medicament therein.

Furthermore and according to another embodiment, the at least one lateral stop member comprises a bearing- or skin engaging surface at its distal end, which substantially extends parallel to the piercing assembly. Axial extension of the at least one lateral stop member is preferably equal or greater than the radius of curvature of a bulged or pinched skin section of a patient. Typically, longitudinal or axial extension of the at least first lateral stop member is large enough that at least a portion of a bulged or pinched skin section gets in direct contact with the lateral stop member in longitudinal, hence axial direction.

According to another preferred embodiment, the guiding and/or adjustment assembly further comprises a second lateral stop member disposed at a lateral distance from the first lateral stop member in order to form a receptacle adapted to receive and/or being adapted to form a bulged or pinched portion of the skin or skin tissue. First and second lateral stop members are arranged such, that the piercing assembly is moveably disposed therebetween, wherein depending on the lateral size of the bulged portion, the piercing assembly is asymmetrically displaced between first and second lateral stop members at a pre-defined lateral distance with respect to the first and/or to the second lateral stop member.

It is of further benefit, when according to another embodiment first and second lateral stop members are pivot mounted with respect to each other in order to form a pair of pliers-like assembly. Preferably, first and second lateral stop members are pivot mounted at a proximal end section, that is opposite to their distally located free end adapted to pinch or squeeze a particular skin section.

In an alternative embodiment it is also conceivable that first and second lateral stop members are pivot mounted in an intermediate section, thus forming a scissor-like pivot-mounted assembly.

By pivot-mounting first and second lateral stop members with respect to each other, a well-defined pinched skin section can be formed particularly adapted for intradermal injection. By providing a pliers-like pinching or squeezing arrangement for establishing or forming a bulged or squeezed skin section, a consistent and non-varying bulge formation of a respective skin section can be attained with the help o the stop members.

In still another embodiment, in a position of use, hence when first and second lateral stop members squeeze a skin portion therebetween, the distal bearing- or skin engaging surfaces of first and second lateral stop members extend substantially parallel with respect to each other and/or with respect to the piercing assembly. By having the bearing- or skin engaging surfaces and the piercing assembly oriented and arranged in a substantially parallel way and by moving the piercing assembly with respect to the stop members in a respective parallel or axial way, penetration of the skin layer of interest can be attained with high precision.

It is of further benefit, when according to another embodiment first and second lateral stop members comprise mutually corresponding interlock means that are adapted to keep first and second stop members in a closed or clamped position or in a position of use. This way, administering of the medicament can be facilitated because a user does no longer have to exert a pinching or squeezing force to the lateral stop members for maintaining the bulged or pinched skin portion. Instead, the user may use a free hand for handling of the injection device in order to dispense the dose. By providing first and second lateral stop- or squeeze members with an interlock means, the guiding assembly may even allow and provide intradermal self-administering of a medicament.

According to a further embodiment, the first and/or the second lateral stop member comprises or comprise a longitudinally extending shaft portion forming or comprising the mount for the injection device. Said shaft portion is preferably integrally formed with the bearing- or skin engaging surface disposed at the distal free end of the lateral stop members. Preferably, first and/or second lateral stop members are made of injection molded thermoplastic material.

The shaft portion may further comprise or provide a handle in order to facilitate the handling and operation of the guiding assembly.

Moreover, according to another embodiment, the shaft portion may further comprise a linear guiding means for the injection device or for its piercing assembly. Preferably, the shaft portion extends parallel to the elongation of the piercing assembly. It therefore preferably points in axial direction.

According to another aspect, the shaft portions and bearing- or skin engaging surfaces of first and second lateral stop members are arranged in an intertwined manner. Hence, shaft portion and distally located bearing surface of first and/or second lateral stop members may extend substantially parallel with respect to each other but with a lateral offset.

The shaft portion is interconnected with the bearing- or skin engaging surface of the stop member by way of an intermediate section comprising a curved or S-shaped profile. Typically, the width of said intermediate section is reduced compared to the distal end of the lateral stop member or its shaft portion. In this way, intermediate and bended or curved sections of first and second stop members may virtually intersect when seen from the side.

In a further preferred embodiment, the intermediate section of first and/or second lateral stop members comprises at least one through opening for receiving the piercing assembly. In this way, the piercing assembly is free to move in axial direction irrespective of the geometry of first and/or second stop members and can be led there through.

In still another embodiment, the injection device can be integrally formed and/or can be slidably mounted to at least one of first and/or second lateral stop members. The injection device may comprise a housing to be mechanically coupled or interconnected with the shaft portion of first and/or second lateral stop members.

In still another and independent aspect the invention also refers to a drug delivery device for injecting a dose of an injectable medicament into the skin of a patient. The drug delivery device comprises a cartridge having an inner volume at least partially filled with the medicament and having a piston serving as a sealing member slidably disposed therein. The drug delivery device further comprises a piercing assembly which is preferably to be brought in fluid connection with the inner volume of the cartridge and further comprises a guiding or adjustment assembly as described above for delivery of the dose of the medicament at a pre-defined depth underneath the surface of the skin.

The guiding assembly provides an effective means to facilitate intradermal injection and supports formation of a bulged skin section, which by re-orienting respective skin layers facilitates intradermal injection and dispensing by making use of a conventional syringe assembly to be operably engaged or coupled with the guiding and/or adjustment assembly.

In another exemplary embodiment, a guiding assembly according to the present invention comprises a mount adapted to receive an injection device, a first gripping member rotatably coupled to the mount, a first lateral stop member coupled to the first gripping member, and a spring biasing the first gripping member in a first angular position relative to the mount.

In an exemplary embodiment, the first lateral stop member includes a distal bearing surface adapted to engage a patient's skin.

In an exemplary embodiment, the injection device is axially movable relative to the mount when coupled to the mount.

In an exemplary embodiment, the guiding assembly further comprises a second gripping member coupled to the mount, wherein the spring biases the first gripping member in the first angular position relative to the second gripping member. A second lateral stop member is coupled to the second gripping member. In the first angular position, the first lateral stop member and the second lateral stop member are adapted to engage a bulged skin portion.

In an exemplary embodiment, the spring is a torsion spring.

In an exemplary embodiment, the first gripping member (48) rotates away from the mount in a second angular position.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in greater detail by making reference to the drawings in which.

DETAILED DESCRIPTION

Figure 1:
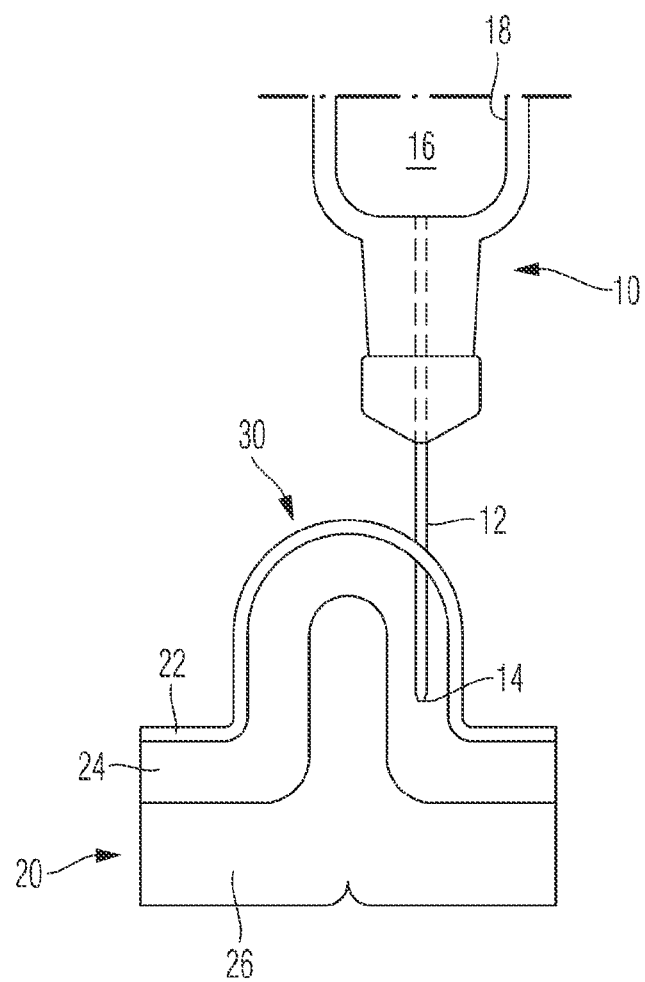
FIG. 1 illustrates the principle of intradermal injection by making use of a bulged or pinched skin portion.

In FIG. 1, a skin portion 20 with various skin layers 22, 24, 26 is illustrated. Here, the upper most skin layer 22 refers to the epidermis while skin layer 24 represents papillary and/or reticular dermis. Some medicaments, in particular some vaccines require intradermal injection. Hence, the distal tip 14 of an injection needle 12 may not penetrate or enter the subcutaneous layer 26. For a precise penetration of the dermal layer 24 it is of benefit to squeeze the respective skin section 20 in order to form a bulged or squeezed skin portion 30 as illustrated in FIG. 1.

Then, at least in the lateral almost upward pointing sections of the bulged region 30, the respective dermal layer 22 extends almost parallel to the orientation of the downward pointing injection needle 12. This way, the penetration depth of the injection needle 12 may vary within a tolerance regime being larger than the thickness of the dermal layer 24. This way, a medicament 16 contained in a barrel or cartridge 18 of an injection device 10 can be precisely injected into the dermal layer 24.

Figure 2:
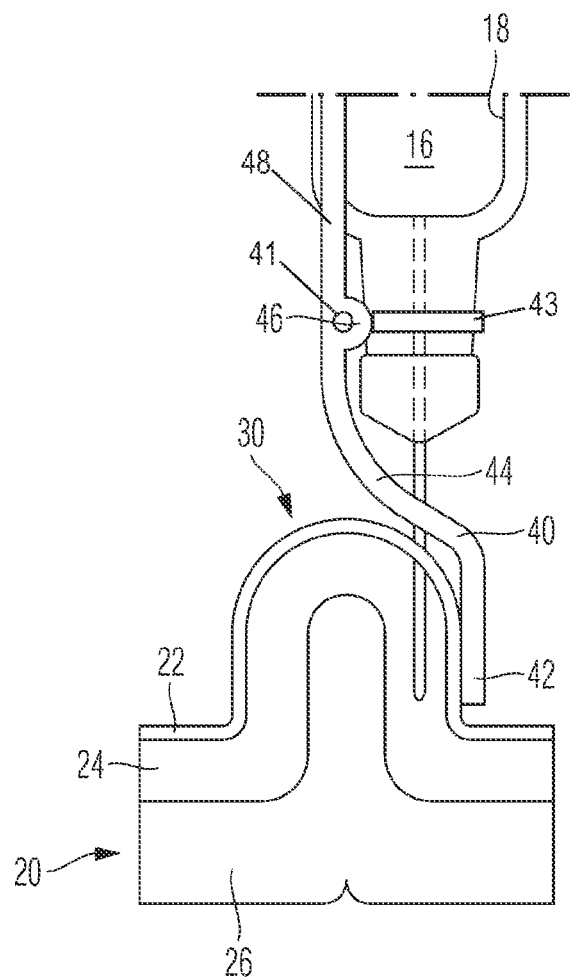
FIG. 2 shows intradermal injection by making use of a guiding assembly having one lateral stop member.

FIG. 2 schematically illustrates a guiding assembly according to an exemplary embodiment of the present invention that helps to form a bulged skin portion 30 as illustrated in FIG. 1. Here, the guiding assembly comprises one lateral stop member 40 having a straight and even shaped lower, hence distal section extending substantially parallel to the injection needle 12. This distal end 42 of the lateral stop member 40 provides a skin engaging or skin bearing surface against which a bulged skin portion 30 is to be pressed. By having the bearing or abutment surface 42 arranged at a pre-defined lateral distance with respect to the position of the injection needle 12, by pressing the bulged skin section 30 against said bearing surface 42, a well-defined penetration of the injection needle 12 into the respective and selected dermal layer 24 can be provided with high precision.

An elongated shaft or gripping member 48 is coupled to the lateral stop member 40. The gripping member 48 and the lateral stop member 40 are rotatable about an interlock means 46 on the guiding assembly. A spring 41 (e.g., a torsion spring) may be used with the interlock means 46 to bias the gripping member 48 and the lateral stop member 40 in a first angular engagement position (as shown in FIG. 2). To release the bulged skin portion 30, the gripping member 48 may be rotated against the bias of the spring 41 to a second angular release position which rotates the lateral stop member 40 away from the bulged skin portion 30.

In the exemplary embodiment shown in FIG. 1 the guiding assembly further includes a collar 43 adapted to receive the injection device 10. For example, the collar 43 may an annular element adapted to engage a distal portion of the injection device 10. For example, if the injection device 10 is a syringe, the collar 43 may engage a neck of the syringe. The collar 43 may include a textured and/or contoured surface to maintain a frictional hold on the injection device 10.

Figure 3:
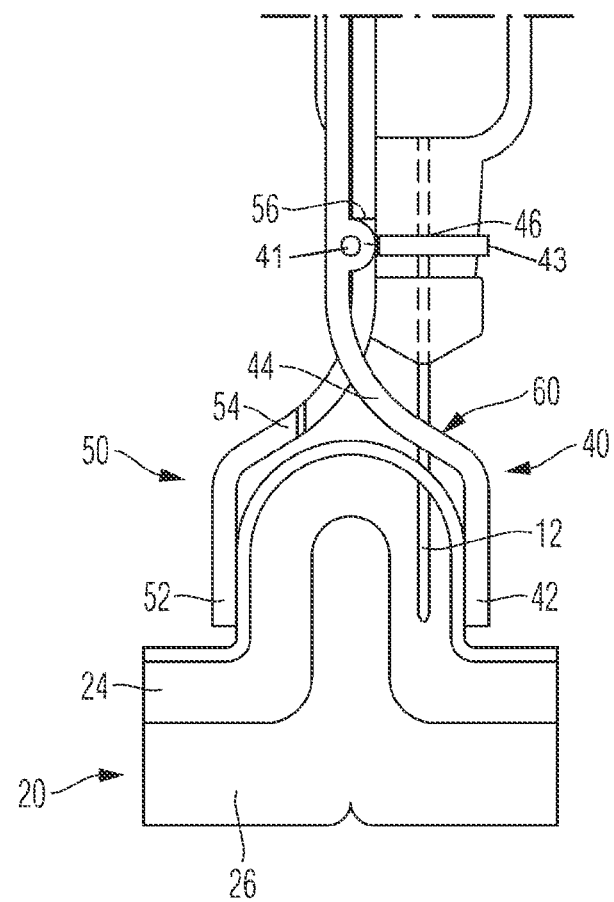
FIG. 3 illustrates another embodiment featuring two lateral stop members.
Figure 4:
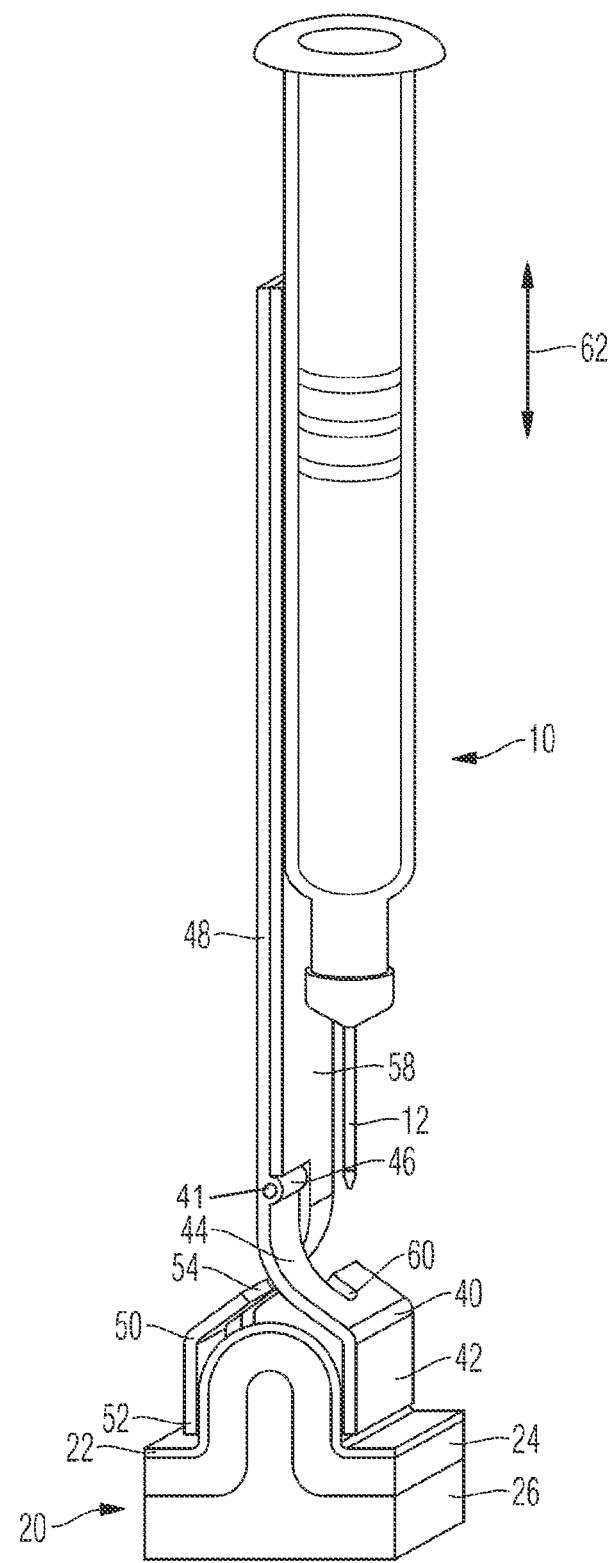
FIG. 4 shows the entire guiding assembly coupled with a syringe-type injection device in a bulge-forming configuration prior to medicament injection and FIG. 5 is illustrative of the embodiment according to FIG. 4 during an injection procedure.
Figure 5:
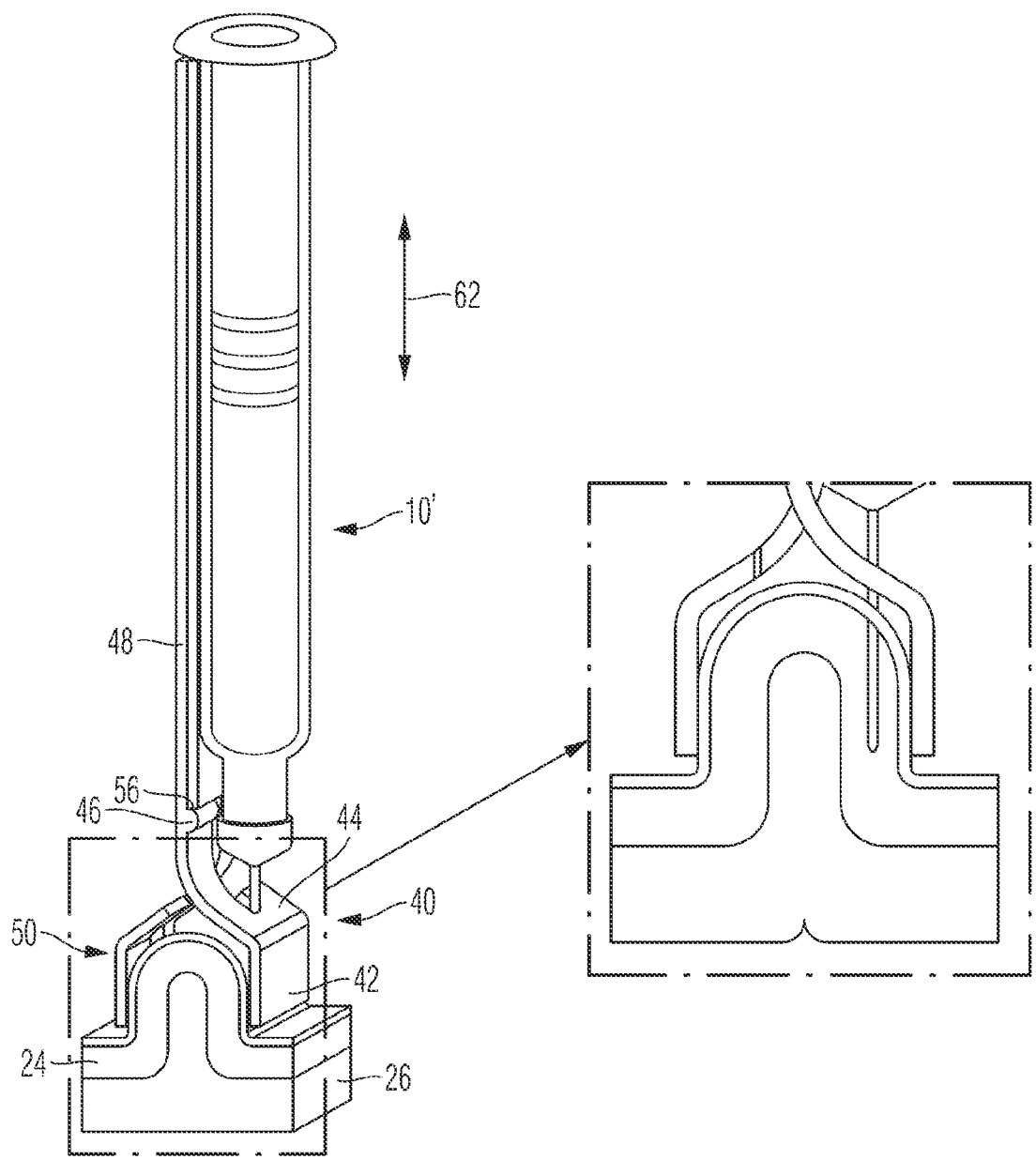

As further illustrated in FIGS. 3 to 5, by way of a second lateral stop member 50, a pliers-like assembly can be attained by way of which the bulged skin section 30 can be formed. As illustrated in FIGS. 4 and 5 the first and second lateral stop members 40, 50 comprise elongated shaft or gripping members 48, 58 that are further provided with mutually engaging interlock means 46, 56. Here, the shaft portion 48 comprises a protrusion 46 inter-engaging with a latching or socket element 56 disposed at the other shaft portion 58. This way, an interlocking clip or a positive engagement of first and second shaft portions 48, 58 can be attained. The interlock means 46, 56 may include the spring 41 to bias the guide assembly in the engagement position, as shown in FIG. 4. Thus, rotating the gripping members 48, 58 against the biasing force of the spring 41 may be necessary to gather and release the bulged skin section 30 before and after the injection, respectively.

Since first and second lateral stop members 40, 50 comprise a symmetrical geometry, their distal end sections 42, 52 form a rather symmetric receptacle for forming a pinched or bulged skin portion 30. By having the drug delivery device 10 axially guided or movably arranged along the shaft portion 58, after pinching or squeezing the skin portion 30 as illustrated in FIG. 4, the drug delivery device or syringe 10 can be longitudinally displaced downward in distal direction 62.

This way, the needle or cannula 12 may enter a through opening 60 formed in an intermediate section 44 of the lateral stop member 40 and may further penetrate and enter the dermal layer 24 as depicted in FIG. 3. As can be further seen from the perspective illustrations of FIGS. 4 and 5, both lateral stop members 40, 50 comprise a S-shaped intermediate sections 44, 54 interconnecting the shaft portions 48, 58 with the respective distally located clamping or skin engaging surfaces or clamping members 42, 52. The enlarged illustration of FIG. 5 identically corresponds to the illustration of FIG. 3 and thus requires no further explanation.

First and second lateral stop members 40, 50 and their respective shaft portions 48, 58 may be interconnected at the uppermost proximal portion, e.g. by way of a film hinge. Moreover, the shaft portion 58 may comprise a longitudinal guiding means in order to slidably dispose the syringe 10 with respect to the guiding assembly in distal or proximal direction 62 as illustrated in FIGS. 4 and 5. The shaft portion 58 may be releasably interconnectable with the syringe 10 or its housing, thus allowing to equip a large variety of different syringes or injection devices with the above described guiding assembly.

Hence, the lateral offset between the bearing of clamping surface 42 and the lateral position or extension of a respective shaft section 48 may vary according to the type of syringe 10 to be used with the guiding assembly. Geometric dimensions of the guiding assembly and its lateral stop members 40, 50 can be designed in such a way, that the lateral distance between an inside surface of the skin engaging distal end 42 and the injection needle 12 corresponds to the intended depth of deposition or depth of injection for the injectable medicament underneath the surface of the skin or dermal tissue 20.

The invention claimed is:

1. A guiding assembly for an injection device, comprising:
a mount adapted to receive the injection device comprising a piercing assembly, the mount being configured such that the piercing assembly is movable along a longitudinal axis of the guiding assembly relative to the mount and extends along the longitudinal axis when the injection device is coupled to the mount;
a first gripping member rotatably coupled to the mount;
a second gripping member coupled to the mount;
a first lateral stop member coupled to the first gripping member, the first lateral stop member comprising a distal bearing surface adapted to engage a surface of skin of a patient and extending along the longitudinal axis of the guiding assembly;
a second lateral stop member coupled to the second gripping member; and
a torsion spring biasing the first gripping member in a first angular position relative to the mount,
wherein when the first gripping member is in the first angular position, the first lateral stop member and the second lateral stop member are adapted to engage the surface of the skin, and
wherein the mount is positioned relative to the first lateral stop member and the second lateral stop member such that the piercing assembly is asymmetrically displaced between the first and second lateral stop members and such that the piercing assembly is displaced at a predefined lateral distance with respect to one of the first and second lateral stop members when the first gripping member is in the first angular position.

2. The guiding assembly according to claim 1, wherein the first gripping member is configured to rotate away from the mount into a second angular position.

3. The guiding assembly according to claim 1, wherein the first lateral stop member comprises a first interlock member engaged with a second interlock member of the second lateral stop member, the first lateral stop member and the first gripping member being rotatable relative to the second lateral stop member and the second gripping member about the second interlock member.

4. The guiding assembly according to claim 3, wherein the longitudinal axis of the guiding assembly extends through the first interlock member and the second interlock member.

5. The guiding assembly according to claim 3, wherein the torsion spring is coupled to at least one of the first and second

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Met Gln Lys Ser Leu Asp Ser
            20                  25                  30

Thr Phe Thr Gly Glu Gly His
        35
``` interlock members to bias the first gripping member in the first angular position relative to the mount.

6. The guiding assembly according to claim 1, wherein the second gripping member extends along the longitudinal axis of the guiding assembly.

7. The guiding assembly according to claim 6, wherein the first gripping member extends along the longitudinal axis of the guiding assembly.

8. The guiding assembly according to claim 6, wherein the second gripping member comprises a guide mechanism configured to slidably couple the injection device to the second gripping member.

9. The guiding assembly according to claim 1, further comprising an intermediate section connecting the second lateral stop member to the second gripping member, the intermediate section comprising a curved profile.

10. The guiding assembly according to claim 9, wherein the intermediate section defines an opening extending through the intermediate section, the opening being positioned to receive the piercing assembly.

11. The guiding assembly according to claim 10, wherein the opening is positioned between the first lateral stop member and the second lateral stop member.

12. The guiding assembly according to claim 11, wherein the opening is positioned beneath the second gripping member.

13. The guiding assembly according to claim 1, wherein the second lateral stop member comprises a distal bearing surface adapted to engage the surface of the skin, the distal bearing surface of the second lateral stop member extending along the longitudinal axis of the guiding assembly and being configured to extend parallel to the piercing assembly when the first gripping member is in the first angular position.

14. The guiding assembly according to claim 13, wherein the first gripping member and the first lateral stop member are intertwined with the second gripping member and the second lateral stop member.

15. The guiding assembly according to claim 13, wherein the distal bearing surface of the first lateral stop member and the distal bearing surface of the second lateral stop member are configured to engage the surface of the skin to form a bulged skin portion when the first gripping member is in the first angular position, the bulged skin portion comprising a portion extending along the longitudinal axis of the guiding assembly.

16. The guiding assembly according to claim 13, wherein the pre-defined lateral distance corresponds to a depth of an intradermal layer of the skin.

17. The guiding assembly according to claim 1, further comprising a collar configured to support a neck portion of the injection device in a lateral direction and a distal direction when the piercing assembly is moved distally along the longitudinal axis of the guiding assembly.

18. The guiding assembly according to claim 1, wherein the second gripping member is adjacent the mount and is configured to be adjacent the injection device when the injection device is coupled to the mount.

19. A drug delivery device for injecting a dose of a medicament into skin of a patient and comprising:
an injection device comprising
a cartridge defining an inner volume containing the medicament and having a piston slidably disposed within the cartridge, and
a piercing assembly extending from the cartridge and being in fluid connection with the inner volume; and
a guiding assembly comprising
a mount adapted to receive the injection device, the mount being configured such that the piercing assembly is movable along a longitudinal axis of the guiding assembly relative to the mount and extending along the longitudinal axis when the injection device is coupled to the mount;
a first gripping member rotatably coupled to the mount;
a second gripping member coupled to the mount;
a first lateral stop member coupled to the first gripping member, the first lateral stop member comprising a distal bearing surface adapted to engage a surface of the skin of the patient and extending along the longitudinal axis of the guiding assembly;
a second lateral stop member coupled to the second gripping member; and
a torsion spring biasing the first gripping member in a first angular position relative to the mount,
wherein when the first gripping member is in the first angular position, the first lateral stop member and the second lateral stop member are adapted to engage the surface of the skin, and
wherein the mount is positioned relative to the first lateral stop member and the second lateral stop member such that the piercing assembly is asymmetrically displaced between the first and second lateral stop members and such that the piercing assembly is displaced at a pre-defined lateral distance with respect to one of the first and second lateral stop members when the first gripping member is in the first angular position.

* * * * *